United States Patent [19]
Tanaka et al.

[11] Patent Number: 5,159,102
[45] Date of Patent: Oct. 27, 1992

[54] 7-THIAPROSTAGLANDINS E, AND PROCESS FOR PRODUCING SAME

[75] Inventors: Toshio Tanaka; Kiyoshi Bannai; Atsuo Hazato, all of Hino; Seizi Kurozumi, Kokubunji, all of Japan

[73] Assignee: Teijin Limited, Saka, Japan

[21] Appl. No.: 526,682

[22] Filed: May 22, 1990

Related U.S. Application Data

[63] Continuation of Ser. No. 120,726, Nov. 13, 1990, abandoned, which is a continuation of Ser. No. 796,571, Oct. 25, 1985, abandoned.

[51] Int. Cl.$^5$ .......................................... C07C 177/00
[52] U.S. Cl. .................................... 560/17; 556/427; 560/118; 560/121; 562/431; 562/498; 562/503
[58] Field of Search .................. 560/17, 118, 121; 562/431, 498, 503; 556/427

[56] References Cited

U.S. PATENT DOCUMENTS 4,466,980  8/1984  Tanaka ........................ 514/530

FOREIGN PATENT DOCUMENTS

| | | | |
|---|---|---|---|
| 25422342 | 2/1979 | Japan . | |
| 257108065 | 7/1982 | Japan . | |
| 110562 | 7/1983 | Japan | 560/121 |
| 029661 | 2/1984 | Japan | 560/121 |
| 25929661 | 2/1984 | Japan . | |
| 61-30569 | 2/1986 | Japan | 560/121 |
| 101458 | 6/1989 | Japan | 560/121 |

Primary Examiner—Robert Gerstl
Attorney, Agent, or Firm—Kenyon & Kenyon

[57] ABSTRACT 7-thiaprostaglandins $E_1$ which are compounds represented by the following formula [I] or their enantiomers or mixtures thereof in any ratio:

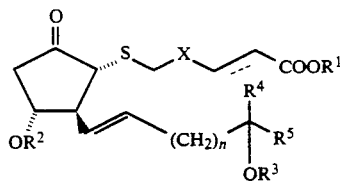

where $R^1$ represents a hydrogen atom, a $C_1$–$C_{10}$ alkyl group, a $C_2$–$C_{20}$ alkenyl group, a substituted or unsubstituted phenyl group, a substituted or unsubstituted $C_3$–$C_{10}$ cycloalkyl group, a substituted or unsubstituted phenyl ($C_1$–$C_2$) alkyl group, or one equivalent cation; $R^2$ and $R^3$, which may be the same or different, represent a hydrogen atom, a tri ($C_1$–$C_7$) hydrocarbon silyl group, or a group forming an acetal linkage together with an oxygen atom of a hydroxyl group; $R^4$ represents a hydrogen atom, a methyl group or a vinyl group; $R^5$ represents a linear or branched $C_3$–$C_8$ alkyl group, a linear or branched $C_3$–$C_8$ alkenyl group, a linear or branched $C_2$–$C_8$ alkynyl group, a phenyl group which may be substituted, a phenoxy group which may be substituted, a $C_3$–$C_{10}$ cycloalkyl group which may be substituted, or a linear or branched $C_1$–$C_5$ alkyl group which may be substituted with a $C_1$–$C_6$ alkoxy group, a phenyl group which may be substituted, a phenoxy group which may be substituted or a $C_3$–$C_{10}$ cycloalkyl group which may be substituted; X represents an ethylene group, a vinylene group or an ethylene group; n represents 0 or 1; the expression ⫽ represents an ethylene group or a vinylene group, provided that when n is o and x is an ethylene group, $R^5$ is not a linear or branched $C_3$–$C_8$ alkyl group or a $C_3$–$C_{10}$ cycloalkyl group which may be substituted.

Such compounds are especially useful for the treatment and prevention of digestive organ diseases such as a duodenal ulcer or a gastric ulcer.

3 Claims, No Drawings

7-THIAPROSTAGLANDINS E, AND PROCESS FOR PRODUCING SAME

This application is a continuation of application Ser. No. 07/120,726, filed Nov. 13, 1990 which is a continuation of Ser. No. 796,571 filed Oct. 25, 1985.

DESCRIPTION

1. Technical Field

The present invention relates to novel 7-thiaprostaglandins $E_1$ and a process for producing the same. More specifically, the present invention relates to novel 7-thiaprostaglandians $E_1$ useful as medicines and a process for producing said 7-thiaprostaglandins $E_1$ which comprises reacting an organolithium compound with a copper compound, then reacting the resultant reaction product with 2-organothio-2-cyclopentenones, and optionally subjecting the resultant product to deprotection, hydrolysis, salt-formation and/or reduction reaction.

2. Background of the Art

Natural prostaglandins are known as local hormones having a biologically and pharmacologically high activity and therefore a large number of studies on their derivatives have been made. Among natural prostaglandins, prostanglandin $E_1$ has strong blood platelet aggregation inhibition effect and vasodilatation effect, etc. and begins to be used for clinical applications.

The greatest defect of natural prostaglandins, especially prostaglandins $E_1$, is that they can not be orally administered because they are rapidly metabolized when orally administered and therefore they must be usually administered by an intravenous injection.

Conventionally, synthetic prostaglandins prepared by replacing one or two carbon atoms forming the skeleton of natural prostaglandins with a sulfur atom have been variously studied.

For example, there are known 1-thiaprostaglandin $E_2$ or $F_{2\alpha}$ wherein the carbon atom at the 1-position of natural prostaglandins is replaced with a sulfur atom (J. Org. Chem., 40, 521, (1975)), 3-thia-11-deoxyprostaglandin $E_1$ (Tetrahedron Letters, 1975, 765; and J. Med. Chem., 20, 1662 (1977)), 7-thiaprostaglandins $F_\alpha$ (J. Amer. Chem. Soc., 96, 6757 (1974)), 9S-prostaglandins $E_1$ (Tetrahedron Letters, 1974, 4267 and 4459; Tetrahedron Letters, 1976, 4793; and Heterocycles, 6, 1097 (1977)), 11-thiaprostaglandins $E_1$ or $F_{1\alpha}$ (Tetrahedron Letters, 1975, 1165), 13-thiaprostaglandins E or F (U.S. Pat. No. 4,080,458 (1978)), and 15-thiaprostaglandins $E_2$ (Tetrahedron Letters, 1977, 1629).

Moreover, there are known 11-deoxy-7-thiaprostaglandins $E_1$ (U.S. Pat. No. 4,180,672), natural type 7-thiaprostaglandins $E_1$ containing a hydroxyl group at the 15-position (U.S. Pat. No. 4,466,980) or non-natural type 15-deoxy-16-hydroxy-3-thiaprostaglandins $E_1$ containing a hydroxyl group at the 16-position (Japanese Unexamined Patent Publication No. 54-22342).

DISCLOSURE OF THE INVENTION

An object of the present invention is to provide novel non-natural type 15-deoxy-16-hydroxy-7-thiaprostaglandins $E_1$ containing a hydroxyl group at the 16-position.

Another object of the present invention is to provide novel natural type 7-thiaprottaglandins $E_1$ containing an unsaturated bond at the 4-position or a specific substituent such as an alkenyl group or an alkynyl group at the 15-position.

A further object of the present invention is to provide novel 7-thiaprostaglandins $E_1$ which are especially useful for the treatment or prevention of digestive organ diseases such as a duodenal ulcer and a gastric ulcer.

A still another object of the present invention is to provide novel 7-thiaprostaglandins $E_1$ which can be orally administered.

A further object of the present invention is to provide a process for producing novel 7-thiaprostaglandins $E_1$ which is excellent for industrial purposes.

Other objects and advantages of the present invention will be apparent from the following descriptions.

The above-mentioned objects and advantages of the present invention are attained by the following 7-thiaprostaglandins $E_1$.

That is, the present invention is 7-thiaprostaglandins $E_1$ which are compounds represented by the following formula [I] or their enantiomers or mixtures thereof in any ratio:

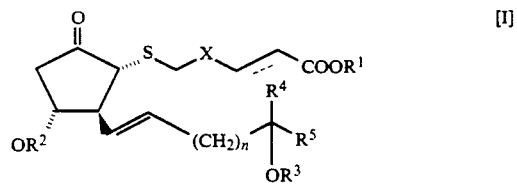

wherein $R^1$ represents a hydrogen atom, a $C_1$–$C_{10}$ alkyl group, a $C_2$–$C_{20}$ alkenyl group, a substituted or unsubstituted phenyl group, a substituted or unsubstituted $C_3$–$C_{10}$ cycloalkyl group, a substituted or unsubstituted phenyl ($C_1$–$C_2$) alkyl group, or one equivalent cation; $R^2$ and $R^3$, which may be the same or different, represent a hydrogen atom, a tri ($C_1$–$C_7$) hydrocarbon silyl group, or a group forming an acetal linkage together with an oxygen atom of a hydroxyl group; $R^4$ represents a hydrogen atom, a methyl group, or a vinyl group; $R^5$ represents a linear or branched $C_3$–$C_8$ alkyl group, a linear or branched $C_3$–$C_8$ alkenyl group, a linear or branched $C_3$–$C_8$ alkynyl group, a phenyl group which may be substituted, a phenoxy group which may be substituted, a $C_3$–$C_{10}$ cycloalkyl group which may be substituted, or a linear or branched $C_1$–$C_5$ alkyl group which is substituted with a $C_1$–$C_6$ alkoxy group, a phenyl group which may be substituted, a phenoxy group which may be substituted, or a $C_3$–$C_{10}$ cycloalkyl group which may be substituted; X represents an ethylene group, a vinylene group or an ethynylene group; n represents 0 or 1, the expression ⫽ represents an ethylene group or a vinylene group; provided that when n is 0 and X is an ethylene group, $R^5$ is not a linear or branched $C_3$–$C_8$ alkyl group or a $C_3$–$C_{10}$ cycloalkyl group which may be substituted.

BEST MODE OF CARRYING OUT THE INVENTION

In the formula [I], $R^1$ represents a hydrogen atom, a $C_1$–$C_{10}$ alkyl group, a $C_2$–$C_{20}$ alkenyl group, a substituted or unsubstituted phenyl group, a substituted or unsubstituted $C_3$–$C_{10}$ cycloalkyl group, a substituted or unsubstituted phenyl ($C_1$–$C_2$) alkyl group, or one equivalent cation.

The $C_1$–$C_{10}$ alkyl groups may be linear on branched and may include, for example, methyl, ethyl, n-propyl, iso-propyl, n-butyl, sec-butyl, tert-butyl, n-pentyl, n-hexyl, n-heptyl, n-octyl, n-nonyl, and n-decyl.

The $C_2$-$C_{20}$ alkenyl groups may include, for example, allyl, isoprenyl, geranyl, citronellyl, and retinyl.

The substituent of the substituted or unsubstituted phenyl is preferably, for example, a halogen atom, a hydroxy group, a $C_2$-$C_7$ acyloxy group, a $C_1$-$C_4$ alkyl group which may be substituted with a halogen atom, a $C_1$-$C_4$ alkoxy group which may be substituted with a halogen atom, a nitrile group, a carboxyl group or a ($C_1$-$C_6$) alkoxycarbonyl group. The halogen atom is, for example, fluorine, chlorine or bromine and particularly preferably fluorine or chlorine. The $C_2$-$C_7$ acyloxy group may include, for example, acetoxy, propionyloxy, n-butyryloxy, iso-butyryloxy, n-valeryloxy iso-valeryloxy, caproyloxy, enanthyloxy or benzoyloxy.

The $C_1$-$C_4$ alkyl groups which may be substituted with a halogen atom may preferably include, for example, methyl, ethyl, n-propyl, iso-propyl, n-butyl, chloromethyl, dichloromethyl, and trifluoromethyl. The $C_1$-$C_4$ alkoxy groups which may be substituted with a halogen atom may preferably include, for example, methoxy, ethoxy, n-propoxy, iso-propoxy, n-butoxy, chloromethoxy, dichloromethoxy and trifluoromethoxy. The ($C_1$-$C_6$) alkoxycarbonyl groups may include, for example, methoxycarbonyl, ethoxycarbonyl, butoxycarbonyl and hexyloxycarbonyl.

The substituted phenyl group may have 1 to 3, preferably one, substituents as mentioned above.

The substituted or unsubstituted $C_3$-$C_{10}$ cycloalkyl groups may be substituted with a similar substituent as mentioned above or may be an unsubstituted cycloalkyl group, such as cyclopropyl, cyclopentyl, cyclohexyl, cycloheptyl, cyclooctyl, and cyclodecyl.

The substituted or unsubstituted phenyl ($C_1$-$C_2$) alkyl groups may be substituted with a similar substituent as mentioned above or may include, for example, unsubstituted benzyl, α-phenethyl and β-phenethyl.

The equivalent cations may include, for example, ammonium cations such as tetramethylammonium, monomethylammonium, dimethylammonium, trimethylammonium, benzylammonium, phenethylammonium, morpholinium cation, monoethanolammonium and piperidinium cation; alkali metal cations such as $Na^+$ and $K^+$; and divalent or trivalent metal cations such as $\frac{1}{2} Ca^{2+}$, $\frac{1}{2} Mg^{2+}$, $\frac{1}{2} Zn^{2+}$ and $\frac{1}{3} Al^{3+}$.

$R^1$ is preferably a hydrogen atom, a $C_1$-$C_{10}$ alkyl group, a $C_2$-$C_{20}$ alkenyl group or one equivalent cation.

In the formula [I], $R^2$ and $R^3$ may be the same or different and represent a hydrogen atom, a tri($C_1$-$C_7$) hydrocarbon silyl group or a group forming an acetal linkage together with an oxygen atom of a hydroxyl group.

The tri ($C_1$-$C_7$) hydrocarbon silyl group may preferably include, for example, a tri ($C_1$-$C_4$) alkylsilyl such as trimethylsilyl, triethylsilyl, and t-butyldimethylsilyl; a diphenyl ($C_1$-$C_4$) alkylsilyl such as t-butyldiphenylsilyl or tribenzylsilyl.

The group forming an acetal linkage together with an oxygen atom of a hydroxyl group may include, for example, methoxyethyl, 1-ethoxyethyl, 2-methoxy-2-propyl, 2-ethoxy-2-propyl, (2-methoxyethoxy) methyl, benzyloxymethyl, 2-tetrahydropyranyl, 2-tetrahydrofuranyl or 6,6-dimethyl-3-oxa-2-oxobicyclo [3.1.0] hexa-4-yl. Of these, 2-tetrahydropyranyl, 2-tetrahydrofuranyl, 1-ethoxyethyl, 2-methoxy-2-propyl, 2-ethoxy-2-propyl, (2-methoxyethoxy) methyl or 6,6-dimethyl-3-oxa-2-oxobicyclo [3.1.0] hexa-4-yl is especially preferable.

As $R^2$ or $R^3$, among the above-mentioned groups, a hydrogen atom, a tri (C ) alkylsilyl group, a diphenyl ($C_1$-$C_4$) alkylsilyl group, a 2-tetrahydropyranyl group, a 2- group, an 1-ethoxyethyl group, a 2-methoxy-2-propyl group, a 2-ethoxy-2-propyl group, a (2-methoxyethoxy) methyl group or a 6,6-dimethyl-3-oxa-2-oxobicyclo [3.1.0] hexa-4-yl group is preferable.

In the formula [I], $R^4$ represents a hydrogen atom, a methyl group or a vinyl group.

In the formula [I], $R^5$ represents a linear or branched $C_3$-$C_8$ alkyl group, a linear or branched $C_3$-$C_8$ alkenyl group, a linear or branched $C_3$-$C_8$ alkynyl group, a phenyl group which may be substituted, a phenoxy group which may be substituted, a $C_3$-$C_{10}$ cycloalkyl group which may be substituted, or a linear or branched $C_1$-$C_5$ alkyl group which may be substituted with a $C_1$-$C_6$ alkoxy group, a phenyl group which may be substituted, a phenoxy group which may be substituted or a $C_3$-$C_{10}$ cycloalkyl group which may be substituted.

The linear or branched $C_3$-$C_8$ alkyl groups may include, for example, n-propyl, n-butyl, n-pentyl, n-hexyl, n-heptyl, n-octyl, 1-methyl-1-butyl, 2-methylhexyl, 2-methyl-2-hexyl, 2-hexyl, 1,1-dimethylpentyl, preferably butyl, pentyl, hexyl, (2R)- or (2S)-2-methylhexyl, 2-hexyl, 1-methyl-1-butyl, 2-methyl-1-butyl, more preferably butyl. A hydrogen atom to be attached to such alkyl groups may be deuterium and tritium.

The linear or branched $C_3$-$C_8$ alkenyl groups may include, for example, 1-butenyl, 2-butenyl, 1-pentenyl, and 2-methyl-4-hexenyl. A hydrogen atom to be attached to such alkenyl groups may be deuterium and tritium.

The linear or branched $C_3$-$C_8$ alkynyl groups may include, for example, 1-butynyl, 2-butynyl, 1-pentynyl, and 2-methyl-4-hexynyl.

The substituent of a phenyl group which may be substituted and a phenoxy group which may be substituted may be a similar substituent as mentioned for the substituent of a substituted phenyl group of $R^1$ the substituent of a $C_3$-$C_7$ cycloalkyl group may be a similar substituent as mentioned for the substituent of a substituted phenyl group of $R^1$. The unsubstituted $C_3$-$C_7$ cycloalkyl group may include, for example, cyclopropyl, cyclopentyl, cyclohexyl, cycloheptyl, cyclooctyl and cyclodecyl.

The $C_1$-$C_6$ alkoxy groups in the linear or branched $C_1$-$C_5$ alkyl group which may be substituted with a $C_1$-$C_6$ alkoxy group, a phenyl group which may be substituted, a phenoxy group which may be substituted or a $C_3$-$C_{10}$ cycloalkyl group which may be substituted may include, for example, methoxy, ethoxy, propoxy, isopropoxy, butoxy, t-butoxy, and hexyloxy. The phenyl group which may be substituted and the phenoxy group which may be substituted may preferably include those mentioned above. The $C_3$-$C_{10}$ cycloalkyl groups which may be substituted may preferably include those mentioned above. The linear or branched $C_1$-$C_5$ alkyl groups may include, for example, methyl, ethyl, n-propyl, iso-propyl, n-butyl, iso-butyl, sec-butyl, t-butyl and pentyl. The substituent may be attached to the alkyl group at any position.

As $R^5$, butyl, pentyl, 1-methyl-1-butyl, 2-methyl-1-butyl, cyclopentyl, cyclohexyl and phenyl are preferable.

In the formula [I], X represents an ethylene group, a vinylene group or an ethynylene group. The vinylene group may be a cis-vinylene group, a trans-vinylene group or mixtures thereof in any ratio.

A hydrogen atom to be attached to such an ethylene group or a vinylene group may be deutrium and tritium. The expression ⫽ represents an ethylene group or a vinylene group. The vinylene group may be a cis-vinylene group, a trans-vinylene group or mixtures thereof in any ratio.

In the formula [I], n represents 0 or 1.

In the formula [I], when n is 0 and X represents an ethylene group, $R^5$ is not a linear or branched $C_3$–$C_8$ alkyl group or a $C_3$–$C_{10}$ cycloalkyl group which may be substituted.

The 7-thiaprostaglandins $E_1$ of the present invention are classified into the following two classes on the basis of the above-mentioned definition of n, X and $R^5$.

(i) 7-thiaprostaglandins $E_1$ in the case of n=1

In the case of n=1, the 7-thiaprostaglandins $E_1$ of the present invention are represented by the following formula [I-1]:

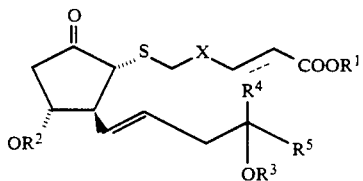

[I-1]

wherein $R^1$, $R^2$, $R^3$, $R^4$, $R^5$, X and the expression ⫽ are the same as defined above. In the case, the 7-thiaprostaglandins $E_1$ are 15-deoxy-16-hydroxy-7-thiaprostaglandins $E_1$.

(ii) 7-thiaprostaglandins $E_1$ in the case of n=0

In the case of n=0, the 7-thiaprostaglandins $E_1$ of the present invention are represented by the following formula [I-2]:

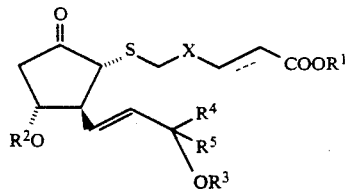

[I-2]

wherein $R^1$, $R^2$, $R^3$, $R^4$, $R^5$, X and the expression ⫽ are the same as defined above, provided that when X is an ethylene group, $R^5$ is not a linear or branched $C_3$–$C_8$ alkyl group or a $C_3$–$C_{10}$ cycloalkyl group which may be substituted. In this case, the 7-thiaprostaglandins $E_1$ contain an unsaturated bond at the 4-position or a substituent such as an alkynyl group or an alkenyl group at the 15-position.

In the compound of the formula [I], the configuration of a substituent attached on the cyclopentanone ring is the same as has natural prostaglandin $E_1$. Therefore, such a stereoisomer is especially useful. The present invention includes stereoisomers which are the enantiomer of the above-mentioned stereoisomer and have the following formula [I] ent, or mixtures thereof in any ratio

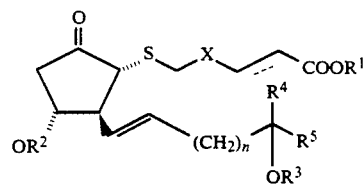

[I] ent wherein $R^1$, $R^2$, $R^3$, $R^4$, $R^5$, n, X and the expression ⫽ the same as defined above. Since the carbon atom to which $OR^3$, $R^4$ and $R^5$ are attached by substitution is an asymmetric carbon atom, two types of optical isomers exist. The present invention includes any of these optical isomers or mixtures thereof in any ratio.

Preferable examples of the novel 7-thiaprostaglandins $E_1$ of the formula [I] which are provided by the present invention may include the following compounds.

(01) 15-deoxy-16-hydroxy-7-thiaprostaglandin $E_1$
(02) 15-deoxy-16-hydroxy-18-oxa-7-thiaprostaglandin $E_1$
(03) 18,19,20-trinor-15-deoxy-16-hydroxy-17-phenoxy-7-thiaprostaglandin $E_1$
(04) 15-deoxy-16-hydroxy-20-methyl-7-thiaprostaglandin $E_1$
(05) 15-deoxy-16-hydroxy-17,20-dimethyl-7-thiaprostaglandin $E_1$
(06) 17,18,19,20-tetranor-15-deoxy-16-hydroxy-16-cyclopentyl-7-thiaprostaglandin $E_1$
(07) 17,18,19,20-tetranor-15-deoxy-16-hydroxy-16-cyclohexyl-7-thiaprostaglandin $E_1$
(08) 15-deoxy-16-hydroxy-16-methyl-7-thiaprostaglandin $E_1$
(09) 15-deoxy-16-hydroxy-16-methyl-18-oxa-7thiaprostaglandin $E_1$
(10) 18,19,20-trinor-15-deoxy-16-hydroxy-17-phenoxy-16-methyl-7-thiaprostaglandin $E_1$
(11) 15-deoxy-16-hydroxy-16,20-dimethyl-7thiaprostaglandin $E_1$
(12) 15-deoxy-16-hydroxy-16,17,20-trimethyl-7thiaprostaglandin $E_1$
(13) 17,18,19,20-tetranor-15-deoxy-16-hydroxy-16-cyclopentyl-16-methyl-7-thiaprostaglandin $E_1$
(14) 17,18,19,20-tetranor-15-deoxy-16-hydroxy-16-cyclohexyl-16-methyl-7-thiaprostaglandin $E_1$
(15) 15-deoxy-16-hydroxy-16-vinyl-7-thiaprostaglandin $E_1$
(16) 15-deoxy-16-hydroxy-16-vinyl-18-oxa-7-thiaprostaglandin $E_1$
(17) 18,19,20-trinor-15-deoxy-16-hydroxy-17-phenoxy-16-vinyl-7-thiaprostaglandin $E_1$
(18) 15-deoxy-16-hydroxy-20-methyl-16-vinyl-7-thiaprostaglandin $E_1$
(19) 15-deoxy-16-hydroxy-17,20-dimethyl-16-vinyl-7-thiaprostaglandin $E_1$
(20) 17,18,19,20-tetranor-15-deoxy-16-hydroxy-16-cyclopentyl-16-vinyl-7-thiaprostaglandin $E_1$
(21) 17,18,19,20-tetranor-15-deoxy-16-hydroxy-16-cyclohexyl-16-vinyl-7-thiaprostaglandin $E_1$
(22) 15-deoxy-2,3-dehydro-16-hydroxy-7-thiaprostaglanding $E_1$
(23) 15-deoxy-2,3-dehydro-16-hydroxy-16-methyl-7-thiaprostaglandin $E_1$

(24) 15-deoxy-2,3-dehydro-16-hydroxy-16-vinyl-7-thia-prostaglandin $E_1$
(25) 4,4,5,5-dehydro-7-thiaprostaglandin $E_1$
(26) 4,4,5,5-dehydro-17-methyl-7-thiaprostaglandin $E_1$
(27) 4,4,5,5-dehydro-17,20-dimethyl-7-thiaprostaglandin $E_1$
(28) 4,4,5,5-dehydro-17(S),20-dimethyl-7-thiaprostaglandin $E_1$
(29) 4,4,5,5-dehydro-17(R),20-dimethyl-7-thiaprostaglandin $E_1$
(30) 4,4,5,5-dehydro-16,17,18,19,20-pentanor-15-cyclohexyl-7-thiaprostaglandin $E_1$
(31) 4,4,5,5-dehydro-16,17,18,19,20-pentanor-15-cyclopentyl-7-thiaprostaglandin $E_1$
(32) 4,4,5,5-dehydro-18-oxa-7-thiaprostaglandin $E_1$
(33) 4,4,5,5-dehydro-17,18,19,20-tetranor-16-cyclohexyl-7-thiaprostaglandin $E_1$
(34) (4E)-4,5-dehydro-7-thiaprostaglandin $E_1$
(35) (4E)-4,5-dehyro-17(R),20-dimethyl-7-thiaprostaglandin $E_1$
(36) (4Z)-4,5-dehydro-7-thiaprostaglandin $E_1$
(37) (4Z)-4,5-dehydro-17(R),20-dimethyl-7-5 thiaprostaglandin $E_1$
(38) 17,17,18,18-dehydro-7-thiaprostaglandin $E_1$
(39) 17,17,18,18-dehydro-16-methyl-7-thiaprostaglandin $E_1$
(40) 18,18,19,19-dehydro-17-methyl-7-thiaprostaglandin $E_1$
(41) 18,18,19,19-dehydro-17,20-dimethyl-7-thiaprostaglandin $E_1$
(42) 19,20-dehydro-17,20-dimethyl-7-thiaprostaglandin $E_1$
(43) 19,20-dehydro-7-thiaprostaglandin $E_1$
(44) 17,18-dehydro-7-thiaprostaglandin $E_1$
(45) The 17,18-deuterated derivative of the compound (38)
(46) The 17,18-tritiated derivative of the compound (39)
(47) The 18,19-tritiated derivative of the compound (41)
(48) The methyl esters of the compounds (1) to (47)
(49) The ethyl esters of the compounds (1) to (47)
(50) The sodium salt of the compounds (1) to (47)

The 7-prostaglandins $E_1$ of the present invention which are compounds of the formula [I] or their enantiomers or mixtures thereof in any ratio are prepared by reacting an organolithium compound of the formula [II]

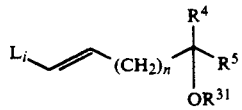

wherein $R^{31}$ represents a tri($C_1$–$C_7$) hydrocarbon silyl group or a group forming an acetal linkage together with an oxygen atom of a hydroxyl group, and $R^4$, $R^5$ and n are the same as defined above, with a copper compound of the formula [III]:

CuQ wherein Q represents a halogen atom, a cyano group, a phenylthio group or a 1-pentyl group, by then reacting the resultant reaction product with 2-organothio-2-cyclopentenones of the following formula [IV] or their enantiomers or mixtures thereof in any ratio:

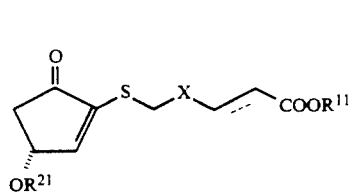

wherein $R^{11}$ represents a $C_1$–$C_{10}$ alkyl group, a $C_2$–$C_{20}$ alkenyl group, a substituted or unsubstituted phenyl group, a substituted or unsubstituted $C_3$–$C_{10}$ cycloalkyl group, or a substituted or unsubstituted phenyl ($C_1$–$C_2$) alkyl group; $R^{21}$ represents a tri($C_1$–$C_7$) hydrocarbon silyl group or a group forming an acetal linkage together with an oxygen atom of a hydroxyl group; and X and the expression ⫽ are the same as defined above, and by optionally subjecting the resultant product to deprotection, hydrolysis, salt-formation and/or reduction reaction.

$R^{31}$ in the organolithium compound of the formula [II] is defined as $R^3$ from which a hydrogen atom is removed. Such an organolithium compound can be prepared by a method known per se (J. Am. Chem. Soc., 94, 7210 (1972); U.S. Pat. Nos. 4,180,672; and 4,466,930; and Japanese Unexamined Patent Publication No. 4,466,930; and Japanese Unexamined Patent Publication (Kokai) No. 53-108929).

Q in the copper compound of the formula [III] represents a halogen atom such as chlorine, fluorine, and bromine, a cyano group, a phenylthio group or a 1-pentyl group. Such a copper compound is a known compound.

$R^{21}$ in the 2-organothio-2-cyclopentenones of the formula [IV] is defined $R^2$ from which a hydrogen atom is removed. $R^{11}$ is defined as $R^1$ from which a hydrogen atom and one equivalent cation are removed.

2-organothio-2-cyclopentenones of the formula [IV-]in which the expression ⫽ is an ethylene group can be prepared by the following synthetic route:

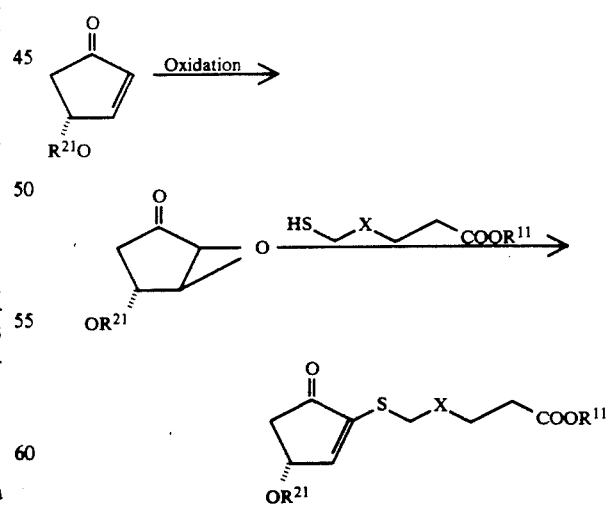

With regard to these synthetic processes, reference will be made to U.S. Pat. Nos. 4,180,672; 4,466,980, etc.

2-Organothio-2-cyclopentenones of the formula [IV-]in which the expression ⫽ is a vinylene group can be prepared by the following synthetic route:

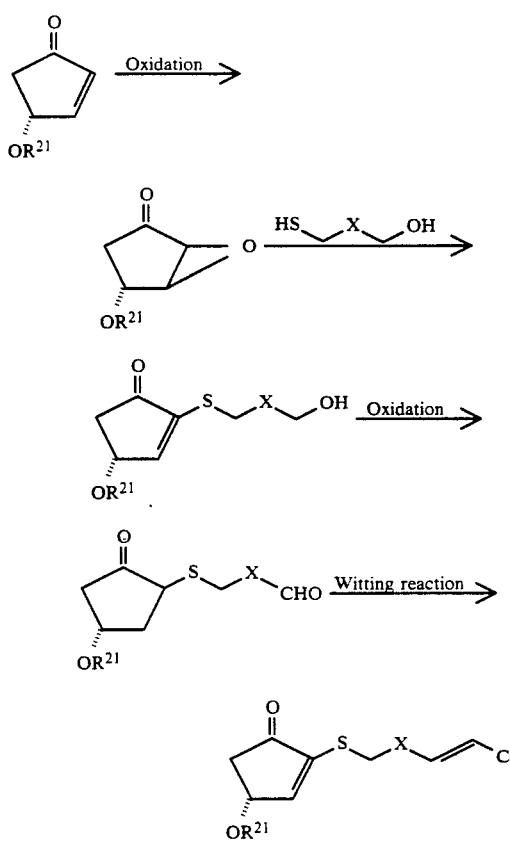

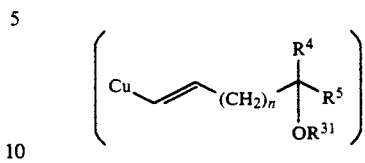

(Tetrahedron Lett., 21, 1247 (1980)).

Then, the above-mentioned reaction product is reacted with the 2-organothio-2-cyclopentenones of the formula [IV]. This reaction is preferably carried out by adding the organothio-2-cyclopentenones to the same reaction system without isolating the reaction product after the reaction of the organolithium compound of the formula [II] and the copper compound of the formula [III].

The 2-organothio-2-cyclopentenones are usually used in an amount of 0.5 to 1.5 times by mole, preferably 0.7 to 1.2 times by mole, based on the organolithium compound of the formula [II].

The reaction temperature is in the range of from $-120°$ C. to $0°$ C., preferably from $-90°$ C. to $-30°$ C. Although the reaction time is variable depending upon the reaction temperature, it is usually 10 minutes to 2 hours.

The reaction is carried out in an atmosphere of nitrogen or argon gas.

In the practice of the reaction, when a trivalent phosphorus compound, e.g., trialkylphosphines (e.g., triethylphosphine, tributylphosphine), trialkyl phosphites (e.g., trimethyl phosphite, triethyl phosphite, triisopropyl phosphite, tri-n-butyl phosphite), hexamethylphosphorustriamide or triphenylphosphine is used, the reaction smoothly proceeds. Especially tributylphosphine and hexamethylphosphorustriamide are preferably used.

Such trivalent organic phosphorus compounds may be added during the reaction of the organolithium compound of the formula [II] and the copper compound of the formula [III].

Thus, there are obtained compounds of the formula [I] in which the hydroxyl group is protected and the carboxylic acid at the 1-position is in the form of an ester. Since the production process of the present invention uses a reaction which proceeds stereospecifically, from the starting material having the configuration represented by the formula [IV], a compound having the configuration represented by the formula [I], is obtained, and from the enantiomer of the formula [IV], an enantiomer of the formula [I] represented by the formula [I]ent is obtained.

At the completion of the reaction, the resultant product is separated from the reaction mixture and purified in a conventional manner. For example, extraction, washing, chromatography or combinations thereof may be used.

Moreover, the compounds as obtained herein wherein the hydroxyl group is protected and the carboxylic acid at the 1-position is in the form of an ester is then optionally subjected to deprotection, hydrolysis or salt-formation reaction.

Alternatively, the compounds may be subjected to a reduction reaction in which X in the formula [I] which is an ethynylene group or a vinylene group is reduced, With regard to these synthetic processes, reference will be made to U.S. Pat. No. 4,466,980.

In the present invention, the organolithium compound of the formula [II] is first reacted with the copper compound of the formula [III]. The reaction is carried out in the presence of an organic medium. An inert non-protonic organic medium which is liquid under the reaction temperature and does not react with the reaction reagents is preferably used.

Such inert non-protonic organic media may include, for example, saturated hydrocarbons such as pentane, hexane, heptane, and cyclohexane; aromatic hydrocarbons such as benzene, toluene, and xylene; ether solvents such as diethyl ether, tetrahydrofuran, dioxane, dimethoxyethane, and diethylene glycol dimethyl ether; and other non-protonic polar solvents such as hexamethylphosphorictriamide (HMP), N,N-dimethylformamide (DMF), N,N-dimethylacetamide (DMAA), dimethyl sulfoxide, sulforan, and N-methylpyrrolidone. These solvents may be used in the form of a mixture of two or more thereof.

The copper compound of the formula [III] is usually used in an amount of 0.8 to 2.0 times by mole, preferably 1 to 1.2 times by mole, based on the organolithium compound of the formula [II].

The reaction temperature is in the range of from $-100°$ C. to $0°$ C., more preferably from approximately $-78°$ C. to $-20°$ C. The reaction time is variable depending on the reaction temperature. Usually, an about one hour reaction time at a temperature of $-78°$ C. to $-40°$ C. is sufficient.

The reaction is preferably carried out in an atmosphere of nitrogen or argon gas.

or to a reduction reaction in which $R^5$ in the formula [I] which is a linear or branched $C_3$-$C_8$ alkenyl group, or a linear or branched $C_3$-$C_8$ alkynyl group is reduced.

The removal of the protective group ($R^{21}$ and $R^{31}$) of a hydroxyl group, when the protective group is a group forming an acetal linkage together with an oxygen atom of a hydroxyl group, is conveniently carried out in a reaction solvent such as water, tetrahydrofuran, ethyl ether, dioxane, acetone, and acetonitrile, in the presence of a catalyst such as acetic acid, the pyridinium p-toluensulfonate or a cation exchange resin. The reaction is usually carried out at a temperature ranging from $-78°$ C. to $+50°$ C. for approximately 10 minutes to 3 days. In the case where the protective group is a tri ($C_1$-$C_7$) hydrocarbon silyl group, the reaction is carried out in the above-mentioned reaction solvents in the presence of a catalyst such as acetic acid, tetrabutylammonium fluoride, cesium fluoride, hydrofluoric acid and hydrogen fluoride-pyridine at the same temperature for the same period.

The removal of the protective group ($R^{11}$) of a carboxy group, i.e., hydrolysis reaction, is carried out in water or a solvent containing water in the presence of an enzyme such as lipase and esterase at a temperature ranging from $-10°$ C. to $+60°$ C. for approximately 10 minutes to 24 hours.

In accordance with the present invention, the compound containing a carboxyl group produced by the hydrolysis reaction is then optionally subjected to a salt-forming reaction to give the corresponding carboxylic acid salt. The salt-forming reaction is known per se, and is carried out by a neutralization reaction with an inorganic compound, such as potassium hydroxide, sodium hydroxide, and sodium carbonate, or an organic basic compound, such as ammonia, trimethylamine, monoethanolamine, and morpholine, in an amount substantially equal to that of the carboxylic acid according to a conventional method.

In the case where an ethynylene group of X in the formula [I] is reduced to an ethylene group or a vinylene group or X is reduced to an ethylene group, and in the case where a $C_3$-$C_8$ alkynyl group of $R^5$ in the formula [I] is reduced to a $C_3$-$C_8$ alkyl group or a $C_3$-$C_8$ alkenyl group of $R^5$ is reduced to a $C_3$-$C_8$ alkyl group, it is preferable to adopt a catalytic reduction method using a hydrogenation catalyst such as a palladium type catalyst, a platinum catalyst, a rhodium catalyst and a ruthenium type catalyst.

The palladium type catalysts include palladium-activated carbon, palladium-calcium carbonate and palladium-barium sulfate. Of these, palladium-activated carbon is preferable.

As the platinum catalyst, there may be used platinum oxides and platinum black.

The rhodium catalyst include chlorotris (triphenylphosphine) rhodium (I).

There is given one example of the reaction conditions hereunder. When palladium-activated carbon is used as a hydrogenation catalyst, ethyl acetate, ethanol or methanol is used as the reaction solvent. A several hours to several days reaction time is usually satisfactory at room temperature under atmospheric pressure.

The present invention has the noticeable feature that when the catalytic reduction is effected in deuterium or tritium, the 7-thiaprostaglandins $E_1$ of the formula [I] labelled with deuterium or tritium are obtained. Such deuterium- or tritium-labelled compounds are useful for the determination of the corresponding 7-thiaprostaglandins $E_1$ useful as a medicine or for the study on the in vivo behaviour of these compounds. The process of the present invention is also useful from this point.

In the case where an ethynylene group of X in the formula [I] is reduced to a vinylene group, or a $C_3$-$C_8$ alkyl group of X is reduced to a $C_3$-$C_8$ alkenyl group, a lindlar catalyst or a palladium-barium sulfate poisoned with quinoline is preferably used.

In the novel 7-thiaprostaglandins $E_1$ represented by the formula [I] which are prepared by the above-mentioned process, the 7-thiaprostaglandins $E_1$ which are compounds of the formula [I'] in which $R^2$ and $R^3$ are hydrogen atoms and their enantiomers or mixtures thereof in any ratio:

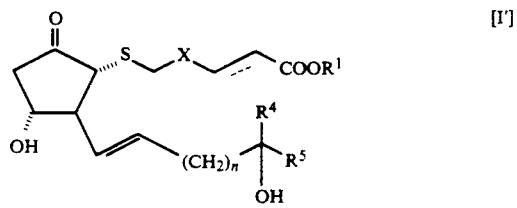

wherein $R^1$, $R^4$, $R^5$, X, n and the expression ⫽ are the same as defined above, have interesting physiological activities and can be used for the prevention and/or treatment of various diseases such as digestive organ diseases, e.g., a duodenal ulcer and a gastric ulcer, liver diseases, e.g., hepatitis, toxipathic hepatitis, fatty liver, hepatic coma, hypertrophy of the liver, and hepatocirrhosis, pancreas, e.g., pancreatitis, arinary diseases, e.g., diabetes kidney diseases, acute kidney insufficiency, cystitis, and urethritis; respiratory diseases, e.g., pneumatic and bronchitis; incretion diseases; immunity diseases, toxicoses, e.g., alcohol poisoning and carbon tetrachloride poisoning and low blood pressure.

The 7-thiaprostaglandins $E_1$ of the present invention are especially useful for the treatment and prevention of digestive organ diseases such as a duodenal ulcer and a gastric ulcer.

The present invention will be explained in more detail by the following examples which by no means limit the present invention.

EXAMPLE 1

Synthesis of (16RS)-15-deoxy-11-t-butyldimethylsilyl-16-t-butyldimethylsilyloxy-7-thiaprostaglandin $E_1$ methyl ester dl-(E)-4-t-butyldimethylsilyloxy-1-iodo-1-octene (1.77 g, 4.8 mmol) was dissolved in ether (10 ml) and cooled to $-78°$ C. Thereafter, t-butyllithium (2.0M, 4.8 ml, 9.6 mmol) was added to the solution and the mixture was stirred at a temperature of $-78°$ C. for 2 hours. Phenylthiocopper (I) (828 mg, 4.8 mmol) and a solution of dexamethylphosphortriamide (1.56 g, 9.6 mmol) in ether (4 ml) were added to the reaction mixture and the resultant mixture was stirred at a temperature of $-78°$ C. for 1 hour. Then, a solution of (4R)-4-t-butyldimethylsilyloxy-2-(5-methoxycarbonylpentylthio)-2-cyclopentenone (1.49 g, 4.0 mmol) in tetrahydrofuran (70 ml) was added to the reaction mixture and the resultant mixture was stirred at a temperature of $-78°$ C. for 15 minutes and at a temperature of $-40°$ C. for 45 minutes.

An acetate buffer solution was added to the reaction mixture. The organic layer was extracted with hexane (150 ml×3), and the separated organic layer was washed with an aqueous sodium chloride, dried over anhydrous magnesium sulfate, filtered and concentrated to obtain 2.44 g of a crude product. The crude product was subjected to silica gel column chromatography (hexane : ethyl acetate=4 : 1) to obtain the desired (16RS)-15-deoxy-11-t-butyldimethylsilyl-16-t-butyl-dimethylsilyloxy-7-thiaprostaglandin $E_1$ methyl ester (2.23 g, 3.63 mmol, 91%).

Nuclear Magnetic Resonance ($CDCl_3$, δ (ppm)); 0.06 (12H, s), 0.87 (21H), 1.1~1.9 (12H, m), 1.9~3.1 (10H, m), 3.61 (3H, s), 3.27~4.4 (2H, m), 5.1~5.7 (2H, m)

Infrared Absorption Spectrum (liquid film, $cm^{-1}$); 1740, 1195, 1165, 960, 830, 770

Mass Spectrometric Analysis (FD-MS); 614 ($M^+$)

EXAMPLE 2

Synthesis of (16RS)-15-deoxy-7-thiaprostaglandin $E_1$ methyl ester

The (16RS)-15-deoxy-11-t-butyldimethylsilyl-16-t-butyldimethylsilyloxy-7-thiaprostaglandin $E_1$ methyl ester (1.20 g, 1.95 mmol) was dissolved in acetonitrile (60 ml). The resultant solution was added with 47% hydrofluoric acid (1 ml) and stirred at room temperature for 1 hour. The reaction mixture was neutralized with an aqueous solution of sodium hydrogen carbonate, and extracted with ethyl acetate (200 ml×3). The separated organic layer was washed with an aqueous sodium chloride solution, dried over anhydrous magnesium sulfate and concentrated to obtain 750 mg of a crude product. The crude product was subjected to silica gel column chromatography (hexane : ethyl acetate=1:3) to obtain the desired (16RS)-15-deoxy-7-thiaprostaglandin $E_1$ methyl ester (680 mg, 176 mmol, 90%).

Nuclear Magnetic Resonance ($CDCl_3$, δ (ppm)); 0.87 (3H, t), 1.1~1.7 (12H, m), 2.0~3.1 (2H, m), 3.61 (3H, s), 3.2~4.5 (2H, m), 5.4~5.75 (2H, m)

Infrared Absorption Spectrum (liquid film, $cm^{-1}$); 3400, 1740, 1260, 845, 730

Mass Spectrometric Analysis (FD-MS): 386 ($M^+$)

High Resolution Mass Spectrometric Analysis; Analytical value: 386, 2102 Calcined value: 386, 2124 ($C_{20}H_{34}O_5S$)

EXAMPLE 3

Synthesis of (16RS)-15-deoxy-11-t-butyl-dimethylsilyl-16-trimethyl-silyloxy-16-methyl-7-thiaprostaglandin $E_1$ methyl ester Dry ether (5 ml) was cooled to −78° C. and was added with a t-butyllithium solution (1.9M, 2.3 ml, 4.4 mmol). A solution of dl-(E)-4-trimethylsilyloxy-4-methyl-1-iodo-1-octene (749 mg, 2.2 mmol) in dry ether (5 ml), which had been cooled to −78° C., was added to the above-prepared solution while stirring at a temperature of −78° C. and the resultant mixture was stirred at a temperature of −78° C. for 1.5 hours Hexamethylphosphortriamide (1.0 ml, 5.5 mmol) was added to phenylthiocopper (I) (380 mg, 2.2 mmol) and the mixture was stirred for 1 hour. Dry tetrahydrofuran (5 ml) was added to the mixture and the resultant mixture was cooled to −78° C. This mixture was added the above-prepared reaction mixture. After the resultant mixture wa stirred at a temperature of −78° C. for 15 minutes, a solution of (4R)-4-t-butyldimethylsilyloxy-2-(5-methoxycarbonylpentylthio)-2-cyclopentenone (745 mg, 2.0 mmol) in dry tetrahydrofuran (20 ml) was added thereto after cooling to −78° C. The resultant mixture was stirred at a temperature of −78° C. for 30 minutes and at a temperature of −40° C. for 1 hour. The reaction mixture was poured in an acetate buffer solution (70 ml) having a pH of 4, followed by stirring for 15 minutes. The resultant solution was added with hexane (50 ml) and filtered through Celite and the filtrate was separated. The aqueous layer was extracted two times with hexane and the extracted organic layers were combined with the organic layer. The mixture was washed once with an aqueous saturated ammonium chloride solution containing aqueous ammonia, twice with an aqueous saturated ammonium chloride solution and twice with an aqueous saturated sodium chloride solution. The washed mixture was dried over anhydrous magnesium sulfate, filtered, concentrated and subjected to silica gel column chromatography (cyclohexane : ethyl acetate=20:1) to obtain (16RS)-15-deoxy-11-t-butyldimethylsilyl-16-trimethylsilyloxy-16-methyl-7-thiaprostaglandin $E_1$ methyl ester (904 mg, 1.54 mmol, 77%).

Nuclear Magnetic Resonance ($CDCl_3$, δ (ppm)); 0.0~0.2 (15H, m), 0.88 (9H, s), 0.7~1.0 (3H, m), 1.18 (3H, s), 1.1~2.0 (12H, m), 2.0~3.1(10H, m), 3.61 (3H, s), 3.8~4.2 (1H, m), 5.2~6.0 (2H, m)

Infrared Absorption Spectrum (liquid film, $cm^{-1}$); 1743, 1248, 835, 773

Mass Spectrometric Analysis (FD-MS); 586 ($M^+$)

EXAMPLE 4

Synthesis or (16RS)-15-deoxy-16-hydroxy-16-methyl-7-thiaprostaglandin $E_1$ methyl ester The (16RS)-15-deoxy-11-t-butyldimethylsilyl-16-trimethylsilyloxy-16-methyl-7-thiaprostaglandin $E_1$ methyl ester (800 mg, 1.36 mmol) obtained in Example 3 was dissolved in acetonitrile (10 ml). To this solution, pyridine (1 ml) and hydrogen fluoride-pyridine (2 ml) were added, and the mixture was stirred at room temperature for 1.5 hours. The reaction mixture was poured on an aqueous saturated sodium hydrogen carbonate solution (70 ml) and the resultant mixture was extracted with ethyl acetate. The aqueous layer was extracted twice with ethyl acetate and the extracted organic layers were combined. The extracted layer was washed with 1N hydrochloric acid, an aqueous solution saturated with sodium hydrogen carbonate and an aqueous saturated sodium chloride solution in that order, and was dried with anhydrous sodium carbonate. After filtration and concentration, the resultant product was subjected to silica gel column chromatography (cyclohexane:ethylacetate:methanol=2 : 2 : 0.04) to obtain the desired (16RS)-15-deoxy-16-hydroxy-16-methyl-7-thiaprostaglandin $E_1$ methyl ester (480 mg, 1.20 mmol, 88%).

Nuclear Magnetic Resonance ($CDCl_3$, δ (ppm)); 0.88 (3H, t), 1.14 (3H, s), 1.0~1.9 (12H, m), 2.0~3.4 (11H, m), 3.61 (3H, s), 3.6~4.5 (2H, m), 5.2~6.0 (2H, m)

Infrared Absorption Spectrum (liquid film, $cm^{-1}$); 3420, 1738

Mass Spectrometric Analysis (FD-MS); 400 ($M^+$)

EXAMPLE 5

Synthesis of (16RS)-15-deoxy-16-hydroxy-16-methyl-7-thiaprostanglandin $E_1$ The (16RS)-15-deoxy-16-hydroxy-16-methyl-7-thiaprostaglandin $E_1$ methyl ester (400 mg, 1.0 mmol) obtained in Example 4 was dissolved in acetone (4 ml). To this solution, a phosphoric acid buffer (40 ml) having a pH of 8 was added, followed by the addition of swine liver esterase (produced by Sigma Co., No. E-3128, pH 8, 0.4 ml). The resultant mixture was stirred at room temperature for 24 hours. After the completion of the reaction, the reaction mixture was acidified to a pH of 4 with 0.1N hydrochloric acid and the aqueous layer was saturated with ammonium sulfate. Thereafter, the aqueous layer was extracted with ethyl acetate and the extract was washed with an aqueous sodium chloride solution. After the washed extract was dried over magnesium sulfate, it was concentrated in vacuo to obtain a crude product. The crude product was subjected to silica gel column chromatography (hexane:ethyl acetate = 1:4, 0.1% acetic acid) to purify it, thereby isolating (16RS)-15-deoxy-16-hydroxy-16-methyl-7-thiaprostaglandin $E_1$ (340 mg, 0.88 mmol, 88%).

Nuclear Magnetic Resonance (CDCl$_3$, δ (ppm)); 0.86 (3H, t), 1.13 (3H, s), 1.0~1.9 (12H, m), 2.0~3.4 (11H, m), 3.6~4.5 (2H, m), 5.2~6.0 (2H, m), 6.23 (1H, bs)

Infrared Absorption Spectrum (liquid film, cm$^{-1}$); 3400, 1740, 1710

EXAMPLE 6

Synthesis of (16RS)-15-deoxy-11-t-butyldimethylsilyl-16-trimethylsilyloxy-16-vinyl-7-thiaprostaglandin $E_1$ methyl ester dl-(E)-4-trimethylsilyloxy-4-vinyl-1-iodo-1-octene (1.79 g, 5.25 mmol), t-butyllithium (1.9M, 5.5 ml, 10.5 mmol), phenylthiocopper (906 mg, 5.25 mmol), and (4R)-4-t-butyldimethylsilyloxy-2-(5-methoxycarbonylpentylthio)-2-cyclopentenone (1.86 g, 5.0 mmol) were reacted according to the same procedures as those described in Example 1 in the same manner as in Example 1. The same post-treatment and column separation as in Example were effected to obtain the desired (16RS)-15-deoxy-11-t-butyldimethylsilyl-16-trimethylsilyloxy-16-vinyl-7-thiaprostaglandin $E_1$ methyl ester (2.72 g, 4.65 mmol, 93%).

Nuclear Magnetic Resonance (CDCl$_3$, δ (ppm)); 0.04 (6H, s), 0.09 (9H, s), 0.85 (12H), 1.1~1.9 (12H, m), 1.9~3.1 (10H, m), 3.63 (3H, s), 3.8~4.2 (1H, m), 4.8~5.6 (5H, m)

Infrared Absorption Spectrum (liquid film, cm$^{-1}$); 3080, 1740, 1250, 835, 775

Mass Spectrometric Analysis (FD-MS), 586 (M$^+$)

EXAMPLE 7

Synthesis of (16RS)-15-deoxy-16-hydroxy-16-vinyl-7-thiaprostaglandin $E_1$ methyl ester The (16RS)-15-deoxy-11-t-butyldimethylsilyl-16-trimethylsilyloxy-16-vinyl-7-thiaprostaglandin $E_1$ methyl ester (1.76 g, 3.0 mmol) obtained in Example 6 was reacted in the same manner as in Example 4. The same post-treatment and column separation as in Example 4 were effected to obtain (16RS)-15-deoxy-16-hydroxy-16-vinyl-7-thiaprostaglandin $E_1$ methyl ester (1.04 g, 2.61 mmol, 87%).

Nuclear Magnetic Resonance (CDCl$_3$, δ (ppm)); 0.87 (3H, t), 1.1~1.7 (12H, m), 2.0~3.1 (12H, m), 3.60 (3H, s), 3.8~4.4 (1H, m), 4.8~5.7 (5H, m)

Infrared Absorption Spectrum (liquid film, cm$^{-1}$); 3400, 3080, 1740, 1160, 1080, 970, 730

Mass Spectrometric Analysis (FD-MS); 400 (M$^+$)

EXAMPLE 8

Synthesis of (16RS)-15-deoxy-2,3-dehydro-11-t-butyldimethylsilyl-16-t-butyldimethylsilyloxy-7-thiaprostaglandin $E_1$ methyl ester dl-(E)-4-t-butyldimethylsilyloxy-1-iodo-1-octene (1.77 g, 4.8 mmol), t-butyllithium (2.0M, 4.8 ml, 9.6 mmol), phenylthiocopper (828 mg, 4.8 mmol), and (4R)-4-t-butyldimethylsilyloxy-2-(5-methoxycarbonyl-4(E)-pentenylthio)-2-cyclopentenone (1.48 g, 4.0 mmol) were reacted according to the same procedures as those described in Example 1 in the same manner as in Example 1. The same post-treatment and column separation as in Example 1 were effected to obtain the desired (16RS)-15-deoxy-2,3-dehydro-11-t-butyldimethylsilyl-16-t-butyldimethylsilyloxy-7-thiaprostaglandin $E_1$ methyl ester (2.18 g, 3.56 mmol, 89%).

Nuclear Magnetic Resonance (CDCl$_3$, δ (ppm)); 0.03 (12H, s), 0.85 (21H), 0.8~2.0 (8H, m), 2.0~3.1 (10H, m), 3.65 (3H, s), 3.3~4.4 (2H, m), 5.1~5.7 (2H, m), 5.80 (1H, d, J=16 Hz), 6.85 (1H, dt, J=16 and 6 Hz). Infrared Absorption Spectrum (liquid film, cm$^{-1}$); 1730, 1660, 1260, 1110, 840, 780

Mass Spectrometric Analysis (FD-MS); 612 (M$^+$)

EXAMPLE 9

Synthesis of (16RS)-15-deoxy-2,3-dehydro-16-hydroxy-7-thiaprostaglandin $E_1$ methyl ester The (16RS)-15-deoxy-2,3-dihydro-11-t-butyldimethylsilll-16-t-butyldimethylsilyloxy-7-thiaprostaglandin $E_1$ methyl ester (1.84 g, 3.0 mmol) was reacted in the same manner as in Example 4. The same post-treatment and column separation as in Example 4 were effected to obtain (16RS)-15-deoxy-2,3-dehydro-16-hydroxy-7-thiaprostaglandin $E_1$ methyl ester (956 mg, 2.49 mmol, 83%).

Nuclear Magnetic Resonance (CDCl$_3$, δ (ppm)); 0.87 (3H), 1.0~2.8 (20H), 3.65 (3H, s), 3.3~4.4 (2H, m), 5.1~5.7 (2H, m), 5.82 (1H, d, J=16 Hz), 6.87 (1H, dt, J=16 and 6 Hz)

Infrared Absorption Spectrum (liquid film, cm$^{-1}$); 3420, 1740, 1720, 1660, 1270, 1080, 975, 730

Mass Spectrometric Analysis (FD-MS); 384 (M$^+$)

EXAMPLE 10

Synthesis of (4Z)-(16RS)-11-t-butyldimethylsilyl-4,5-dehydro-15-deoxy-16-methyl-16-trimethylsilyloxy-7-thiaprostaglandin $E_1$ methyl ester In the same manner as in Example 1, from dl-(E)-4-trimethylsilyloxy-1-iodo-1-octene, and (R)-4-t-butyldimethylsilyloxy-2-((Z)-5-methoxycarbonyl-2-pentenylthio)-2-cyclopentenone, (4Z)-(16RS)-11-t-butyldimethylsilyl-4,5-dehydro-15-deoxy-16-methyl-16-trimethylsilyloxy-7-thiaprostaglandin $E_1$ methyl ester was obtained in a yield of 79%.

Nuclear Magnetic Resonance (CDCl$_3$, δ (ppm));
0.0~0.2 (15H, m), 0.87 (9H, s), 0.7~1.0 (3H, m), 1.18
(3H, s), 1.1~2.0 (6H, m), 2.0~3.1 (12H, m), 3.61 (3H, s),
1.1~2.0 (6H, m), 2.0~3.1 (12H, m), 3.61 (3H, s),
3.8~4.2 (1H, m), 5.2~6.0 (4H, m)

Infrared Absorption Spectrum (liquid film, cm$^{-1}$);
3080, 1740, 1250, 835, 775

Mass Spectrometric Analysis (FD-MS); 584 (M$^+$)

EXAMPLE 11

Synthesis of
(4Z)-(16RS)-4,5-dehydro-15-deoxy-16-hydroxy-16-methyl-7-thiaprostaglandin E$_1$ methyl ester The
(4Z)-(16RS)-11-t-butyldimethylsilyl-4,5-dehydro-15-deoxy-16-methyl-16-trimethylsilyloxy-7--thiaprostaglandin E$_1$ methyl ester obtained in Example 10 was subjected to exactly the same deprotection, post-treatment and purification, so as to obtain (4Z)-(16RS)-4,5-dehydro-15-deoxy-16- hydroxy-16-methyl-7-thiaprostaglandin E$_1$ methyl ester in a yield of 83%.

Nuclear Magnetic Resonance (CDCl$_3$, δ (ppm)); 0.88 (3H, t), 1.14 (3H, S), 1.1~2.0 (6H, m), 2.0~3.4 (14H, m), 3.61 (3H, s), 3.6~4.5 (2H, m), 5.2~6.0 (4H, m)

Infrared Absorption Spectrum (liquid film, cm$^{-1}$); 3420, 1740, 1260, 845, 730

Mass Spectrometric Analysis (FD-MS); 398 (M$^+$)

EXAMPLE 12

Synthesis of
(16S)-15-deoxy-16-hydroxy-16-methyl-7-thiaprostaglandin E$_1$ methyl ester Exactly the same manner as in Example 3 was repeated except that (1E)-(4S)-4-trimethylsilyloxy-4-methyl-1-iodo-1-octene ([α]$^{24}$+1.6° (C=0.62, CHCl$_3$)) was used in place of the dl-(E)-4-trimethylsilyloxy-4-methyl-1-iodo-1-octene. Thus, (16S)-15-deoxy-11-t-butyldimethylsilyl-16-trimethylsilyloxy-16-methyl-7-thiaprostaglandin E$_1$ methyl ester (82%) was obtained. The spectral data of this product agreed with those of the product of Example 3.

Then, the above-mentioned product was subjected to exactly the same deprotection method as in Example 4 to obtain (16S)-15-deoxy-16-hydroxy-16-methyl-7-thiaprostaglandin E$_1$ methyl ester (91%). The spectral data of this product agreed with those of the product of Example 4.

EXAMPLE 13

Synthesis of
(16R)-15-deoxy-16-hydroxy-16-methyl-7-thiaprostaglandin E$_1$ methyl ester Exactly the same manner as in Example 3 was repeated except that (1E)-(4R)-4-trimethylsilyloxy-4-methyl-1-iodo-1octene ([α]$^{24}$−1.6° (C=0.59, CHCl$_3$)) was used in place of the dl-(E)-4-trimethylsilyloxy-4-methyl-1-iodo-1-octene. Thus, (16R)-15-deoxy-11-t-butyldimethylsilyl-16-trimethylsilyloxy-16-methyl-7-thiaprostaglandin E$_1$ methyl ester (87%) was obtained. The spectral data of this product agreed with those of the product of Example 3.

Then, the above-mentioned product was subjected to exactly the same deprotection method as in Example 4 to obtain (16R)-15-deoxy-16-hydroxy-16-methyl-7-thiaprostaglandin E$_1$ methyl ester (86%). The spectral data of this product agreed with those of the product of Example 4.

EXAMPLE 14

Synthesis of
11,15-bis(t-butyldimethylsilyl)-4,4,5,5-dehydro-7-thiaprostaglandin E$_1$ methyl ester (E)-(3S)-t-butyldimethylsilyloxy-1-iodo-1-octene (4.39 g, 11.94 mmol) was dissolved in ether (20 ml) and cooled to −78° C. Then, t-butyllithium (1.9M, 12.9 ml, 23.9 mmol) was added to the solution and the resultant mixture was stirred at a temperature of −78° C. for 2 hours. Phenylthiocopper (2.06 g, 11.94 mmol) and a solution of hexamethylphosphorustriamide (5.84 g, 35.8 mmol) in ether (20 ml) were added to the reaction mixture, and the resultant mixture was stirred at a temperature of −78° C. for 1 hour. Then, a solution of pentynylthio)-2-cyclopentenone (R)-4-t-butyldimethylsilyloxy-2-(5-methoxycarbonyl-2-cyclopentenone (3.95 g, 10.7 mmol) in tetrahydrofuran (50 ml) was added to the above mixture, and the resultant mixture was stirred at a temperature of −78° C. for 15 minutes and at a temperature of −40° C. for 30 minutes.

The reaction mixture was added with a 2M acetate buffer solution and was extracted with hexane (150 ml×3). Each organic layer was washed with an aqueous sodium chloride solution, dried over anhydrous magnesium sulfate, filtered and concentrated so as to obtain 6.8 g of a crude product. The crude product was subjected to silica gel column chromatography (hexane:ethyl acetate=4:1) to obtain the desired 11,15-bis(t-butyldimethylsilyl)-4,4,5,5-dehydro-7-thiaprostaglandin E$_1$ methyl ester (6.83 g, 11.2 mmol, 94%).

Nuclear Magnetic Resonance (CDCl$_3$, δ (ppm)); 0.06 (12H, s, 0.87 (21H), 1.0~1.8 (8H, m), 2.3~3.6 (10H, m), 3.67 (3H, s) 3.80~4.40 (2H, m), 5.50~5.75 (2H, m)

Infrared Absorption Spectrum (liquid film, cm$^{-1}$); 1745, 1250, 1165, 1110, 1075, 965, 885, 835, 805, 775

Mass Spectrometric Analysis (FD-MS); 610 (M$^+$)

EXAMPLE 15

Synthesis of 4,4,5,5-dehydro-7-thiaprostaglandin E$_1$ methyl ester

The 11,15-bis(t-butyldimethylsilyl)-4,4,5,5-dehydro-7-thiaprostaglandin E$_1$ methyl ester (1.22 g, 2.0 mmol) obtained in Example 14 was dissolved in acetonitrile (50 ml). To this solution, pyridine (1.0 ml) and then hydrogen fluoride-pyridine (2.0 ml) were added, and the resultant mixture was stirred at room temperature for 3 hours. The reaction mixture was neutralized with an aqueous solution of sodium hydrogen carbonate, and extracted with ethyl acetate (150 ml×3). Each of the separated organic layers was washed with an aqueous sodium chloride solution, dried over anhydrous magnesium sulfate and concentrated to obtain 780 mg of a crude product. The crude product was subjected to silica gel column chromatography (hexane:ethyl acetate=1:3) to obtain the desired 4,4,5,5-dehydro-7-thiaprostaglandin E$_1$ methyl ester (710 mg, 1.86 mmol, 93%).

Nuclear Magnetic Resonance (CDCl$_3$, δ (ppm)); 0.7~1.0 (3H, m), 1.0~1.8 (8H, m), 2.3~3.5 (12H, m), 3.67 (3H, s) 3.8~4.4 (2H, m), 5.6~5.8 (2H, m)

Infrared Absorption Spectrum (liquid film, cm$^{-1}$); 3400, 1740, 1260, 845, 730

Mass Spectrometric Analysis (FD-MS); 382 (M$^+$)

EXAMPLE 16

Synthesis of 11,15-bis(t-butyldimethylsilyl)-4,4,5,5-dehydro-17(R),20-dimethyl-7-thiaprostaglandin $E_1$ methyl ester The same procedures as those described in Example 14 were repeated except that (E)-(3S, 5R)-3-t-butyldimethylsilyloxy-5-methyl-1-iodo-1-nonen was used in place of the (E)-(3S)-t-butyldimethylsilyloxy-1-iodo-1-octene, and 1-pentynylcopper was used in place of the phenylthiocopper. Thus, 11,15-bis(t-butyldimethylsilyl)-4,4,5,5-dehydro-17(R), 20-dimethyl-7-thiaprostaglandin $E_1$ methyl ester was obtained in a yield of 89%.

Nuclear Magnetic Resonance (CDCl$_3$, δ (ppm)); 0.06 (12H, s) 0.87 (24H), 1.0~1.8 (9H, m), 2.3~3.6 (10H, m), 3.67 (3H, s), 3.85~4.35 (2H, m), 5.50~5.75 (2H, m)

Infrared Absorption Spectrum (liquid film, cm$^{-1}$); 1745, 1250, 1165, 1110, 1075, 965, 885, 835, 805, 775

Mass Spectrometric Analysis (FD-MS); 638 (M$^+$), 581 (M-57), 57

EXAMPLE 17

Synthesis of 4,4,5,5-dehydro-17(R),20-dimethyl-7-thiaprostaglandin $E_1$ methyl ester The 11,15-bis(t-butyldimethylsilyloxy)-4,4,5,5-dehydro-17(R), 20-dimethyl-7-thiaprostaglandin $E_1$ methyl ester obtained in Example 16 was subjected to exactly the same deprotection reaction, post-treatment and purification as those described in Example 2, so as to obtain 4,4,5,5-dehydro-17(R),20-dimethyl-7-thiaprostaglandin $E_1$ methyl ester in a yield of 79%.

Nuclear Magnetic Resonance (CDCl$_3$, δ (ppm)); 0.7~1.0 (6H, m), 1.0~1.9 (9H, m), 2.3~3.5 (12H, m), 3.67 (3H, s) 3.8~4.4 (2H, m), 5.6~5.8 (2H, m).

Infrared Absorption Spectrum (liquid film, cm$^{-1}$); 3400, 1740, 1240, 1200, 1165, 1075, 1040, 965, 735.

Mass Spectrometric Analysis (FD-MS); 410 (M$^+$)

EXAMPLE 18

Synthesis of (4E)-11,15-bis(t-butyldimethylsilyl)-4,5-dehydro-16,17,18,19,20-pentanor-15-cyclohexyl-7-thiaprostaglandin $E_1$ methyl ester According to the same manner as in Example 14, from (E)-(3S)-t-butyldimethylsilyloxy-3-cyclohexyl-1-iodo-1- propene and (R)-4-t-butyldimethylsilyloxy-2-((E)-5-methoxycarbonyl-2-pentenylthio)-2-cyclopentenone, (4E)-11,15-bis(t-butyldimethylsilyl)-4,5-dehydro-16,17,18,19,20-pentanol-15-cyclohexyl-7-thiaprostaglandin $E_1$ methyl ester was obtained in a yield of 87%.

Nuclear Magnetic Resonance (CDCl$_3$, δ (ppm)); 0.06 (12H, s), 0.87 (18H, s), 0.8~1.9 (11H, m), 1.9~3.1 (10H, m), 3.7~4.3 (2H, m), 3.65 (3H, s), 5.2~5.8 (4H, m).

Infrared Absorption Spectrum (liquid film, cm$^{-1}$); 3080, 1740, 1270, 1200, 1080, 975, 885, 835, 805, 775.

Mass Spectrometric Analysis (FD-MS); 624 (M$^+$)

EXAMPLE 19

Synthesis of (4E)-4,5-dehydro-16,17,18,19,20-pentanor-15-cyclohexyl-7-thiaprostaglandin $E_1$ methyl ester The (4E)-11,15-bis(t-butyldimethylsilyl)-4,5- dehydro-16,17,18,19,20-pentanor-15-cyclohexyl-7-thiaprostaglandin $E_1$ methyl ester obtained in Example 18 was subjected to exactly the same deprotection, post-treatment and purification as those described in Example 15, so as to obtain (4E)-4,5-dehydro-16,17,18,19,20-pentanor-15-cyclohexyl-7-thiaprostaglandin $E_1$ methyl ester in a yield of 86%.

Nuclear Magnetic Resonance (CDCl$_3$, δ (ppm)); 0.8~1.9 (11H, m), 1.9~3.2 (12H, m), 3.7~4.3 (2H, m), 3.63 (3H, s), 5.2~5.8 (4H, m)

Infrared Absorption Spectrum (liquid film, cm$^{-1}$); 3420, 3080, 1740, 1270, 1200, 1080, 975, 910, 730.

Mass Spectrometric Analysis (FD-MS); 396 (M$^{-1}$).

EXAMPLE 20

Synthesis of (4Z)-11,15-bis(t-butyldimethylsilyl)-4,5-dehydro-7-thiaprostaglandin $E_1$ methyl ester 7-thiaprostaglandin The 11,15-bis(t-butyldimethylsilyl)-4,4,5,5-dehydro-7-thiaprostaglandin $E_1$ methyl ester (610 mg, 1.0 mmol) obtained in Example 14 was dissolved in ethyl acetate (10 ml). The solution was added with 50 mg of a lindlar catalyst and was stirred at room temperature for 24 hours. The catalyst was filtered off and the reaction mixture was washed with ethyl acetate and concentrated to obtain a crude product. The crude product was subjected to silica gel column chromatography (hexane:ethyl acetate=4:1) so as to obtain the desired (4Z)-11,15-bis(t-butyl-dimethylsilyl)-4,5-dehydro-7-thiaprostaglandin $E_1$ methyl ester (428 mg, 0.70 mmol, 70%).

Nuclear Magnetic Resonance (CDCl$_3$, δ (ppm)); 0.06 (12H, s), 0.87 (3H, s), 1.0~1.8 (8H, m), 2.3~3.6 (10H, m), 3.67 (3H, s), 3.8~4.4 (2H, m), 5.2~5.8 (4H, m).

Absorption Spectrum (liquid film, cm$^{-1}$); 1745, 1250, 1165, 1110, 1075, 965, 885, 835, 805, 775.

Mass Spectrometric Analysis (FD-MS); 612 (M$^+$).

EXAMPLE 21

Synthesis of (4Z)-4,5-dehydro-7-thiaprostaglandin $E_1$ methyl ester

The (4Z)-11,15-bis(t-butyldimethylsilyl)-4,5-dehydro-7-thiaprostaglandin $E_1$ methyl ester (306 mg, 0.5 mmol) obtained in Example 20 was subjected to exactly the same deprotection, post-treatment and purification as those described in Example 2, so as to obtain (4Z)-4,5-dehydro-7-thiaprostaglandin $E_1$ methyl ester (177 mg, 0.46 mmol, 92%).

Nuclear Magnetic Resonance (CDCl$_3$, δ (ppm)); 0.88 (3H, t), 1.0~1.8 (8H, m), 2.2~3.6 (12H, m), 3.63 (3H, s), 3.8~4.4 (2H, m), 5.2~5.8 (4H, m)

Infrared Absorption Spectrum (liquid film, cm$^{-1}$); 3400, 1740, 1260, 845, 730.

Mass Spectrometric Analysis (FD-MS); 384 (M$^+$)

EXAMPLE 22

Synthesis of 4,4,5,5-dehydro-7-thiaprostaglandin $E_1$

The 4,4,5,5-dehydro-7-thiaprostaglandin $E_1$ methyl ester (191 mg, 0.5 mmol) obtained in Example 15 was dissolved in acetone (2 ml). To this solution, a phosphoric acid buffer solution (20 ml) having a pH of 8 was added and then, swine liver esterase (produced by Sigma Co., No. E-3128, pH 8, 0.2 ml) was added. The resultant mixture was stirred at room temperature for 24 hours. After the completion of the reaction, the reaction mixture was acidified to a pH of 4 with 0.1N hydrochloric acid. After the aqueous layer was saturated with ammonium sulfate, it was extracted with ethyl acetate and the extract was washed with an aqueous sodium chloride solution. The organic layer was dried over magnesium sulfate and concentrated in vacuo to obtain a crude product. The crude product was subjected to silica gel column chromatography (hexane:ethyl acetate=1:4, 0.1% acetic acid) to purify it, thereby obtaining 4,4,5,5-dehydro-7-thiaprostaglandin $E_1$ (162 mg, 0.44 mmol, 88%).

Nuclear Magnetic Resonance ($CDCl_3$, δ (ppm)); 0.7~1.0 (3H, m), 1.0~1.8 (8H, m), 2.3~3.5 (10H, m), 3.8~4.4 (2H, m), 5.6~5.8 (2H, m), 6.30 (3H, bs).

Infrared Absorption Spectrum (liquid film, $cm^{-1}$); 3400, 1740, 1710.

Mass Spectrometric Spectrum (FD-MS); 368 (M+)

EXAMPLE 23

Synthesis of (4Z)-4,5-dehydro-7-thiaprostaglandin $E_1$

The (4Z)-4,5-dehydro-7-thiaprostaglandin $E_1$ methyl ester obtained in Example 21 was subjected to exactly the same hydrolysis method as in Example 22, so as to obtain the corresponding (4Z)-4,5-dehydro-7-thiaprostaglandin $E_1$ in a yield of 87%.

Nuclear Magnetic Resonance ($CDCl_3$, δ (ppm)); 0.88 (3H, t), 1.0~1.8 (8H, m), 2.2~3.6 (10H, m), 3.8~4.4 (2H, m), 5.2~5.8 (4H, m), 6.50 (3H, bs).

Infrared Absorption Spectrum (liquid film, $cm^{-1}$); 3400, 1740, 1710.

Mass Spectrometric Analysis (FD-MS); 370 (M+).

EXAMPLE 24

Synthesis of (17R),20-dimethyl-7-thiaprostaglandin $E_1$-4,4,5,5-$d_4$ methyl ester 11,15-bis(t-butyldimethylsilyl)-4,4,5,5-dehydro-(17R), 20-dimethyl-7-thiaprostaglandin $E_1$ methyl ester, which was used as the starting material, was catalytically reduced with deuterium in the presence of a hydrogenation catalyst consisting of 10% palladium-activated carbon. The resultant product was subjected to deprotection to obtain (17R), 20-dimethyl-7-thiaprostaglandin $E_1$-4,4,5,5-$d_4$ methyl ester.

EXAMPLE 25

Synthesis of (17R),20-dimethyl-7-thiaprostaglandin $E_1$-4,4,5,5-$t_4$ methyl ester 11,15-bis(t-butyldimethylsilyl)-4,4,5,5-dehydro-(17R),20-dimethyl-7-thiaprostaglandin $E_1$ methyl ester, which was used as the starting material, was catalytically reduced with tritium in the presence of a hydrogenation catalyst consisting of 10% palladium-activated carbon. Thus, (17R),20-dimethyl-7-thiaprostaglandin $E_1$-4,4,5,5-$t_4$ methyl ester was obtained.

EXAMPLE 26

Synthesis of 19,20-dehydro-17,20-dimethyl-11,15-bis(t-butyl-dimethylsilyl)-7-thiaprostaglandin $E_1$ methyl ester (i) A solution of 2.2M t-butyllithium in pentane (1.6 ml, 3.48 mmol) was added to a solution of 686 mg of (1E, 3S, 5R)-1-iodo-5-methyl-1,7-nonadiene-3-ol t-butyldimethylsilylether in ether (5 ml) at a temperature of −78° C. The resultant solution was stirred for 2 hours. Hexamethylphosphorustriamide (567 mg, 3.48 mmol) was added to a suspension of phenylthiocopper (I) (300 mg, 1.74 mmol) in ether (2 ml) and the mixture was stirred at room temperature until a uniform solution was obtained. Then, this uniform solution was added to the above-prepared solution, and the mixture was stirred at a temperature of −78° C. for 1 hour. To this solution, a solution of 4(R)-t-butyldimethylsilylexy-2-(5-methoxycarbonylpentylthio)-2-cyclopentenone (647 mg, 1.74 mmol) in tetrahydrofuran (20 ml) was added, and the mixture was reacted at a temperature of −78° C. for 15 minutes and at a temperature of −40° C. for 1 hour. After the completion of the reaction, an aqueous ammonium chloride solution containing ammonia was added to the reaction mixture. The aqueous layer was extracted with ether (100 ml×3) and the extract was washed with an aqueous ammonium chloride solution, dried ($MgSO_4$) and concentrated to obtain a crude product. The crude product was subjected to column chromatography to purify it. Thus, 990 mg (yield 89%) of (17R)-19,20-dehydro-17,20-dimethyl-11,15-bis(t-butyldimethylsilyl)-7-thiaprostaglandin $E_1$ methyl ester was obtained in the 5% ethyl acetate-n-hexane eluate fraction. (The configuration of the $\Delta^{19}$-double bond of this product contained 80 to 90% of Z-form.

Nuclear Magnetic Resonance ($CDCl_3$, S(ppm)); 0.88 (21H, bs), 3.65 (3H, S), 3.8~4.4 (2H, m), 5.2~5.7 (4H, m).

Infrared Absorption Spectrum (liquid film, $cm^{-1}$); 1740, 1252, 1110, 965, 882, 835, 775.

Mass Spectrometric Analysis (EI, m/e), 583 (M-tBu), 441, 381, 347, (ii) Similarly, from (1E, 3S, 5R)-1-iodo-5-methyl-1,7-nonadiene-3-ol-t-butyldimethyl ether, (17S)-19,20-dehydro-17,20-dimethyl-11,15-bis(t-butyldimethylsilyl)-7-thiaprostaglandin $E_1$ methyl ester was obtained.

Nuclear Magnetic Resonance ($CDCl_3$, S(ppm)); 0.88 (21H, bs), 3.66 (3H, S), 3.8~4.4 (2H, m), 5.2618 5.7 (4H, m)

In Frared Absorption Spectrum (liquid film, $cm^{-1}$); 1740, 1252, 1110, 965, 882, 835, 775.

Mass Spetrometric Analysis (EI, m/e); 583 (M-tBu), 441.

EXAMPLE 27

Synthesis of 19,20-dehydro-17,20-dimethyl-7-thiaprostaglandin $E_1$ methyl ester (i) 640 mg of the (17R)-19,20-dehydro-17,20-dimethyl-11,15-bis(t-butyldimethylsilyl)-7-thiaprostaglandin $E_1$ methyl ester obtained in Example 26 was dissolved in acetonitrile (20 ml). To this solution, 0.9 ml of pyridine and then 17 ml of pyridinium poly(hydrogen fluoride) were added. The resultant mixture was stirred at room temperature for 2 hours. The reaction mixture was neutralized with an aqueous solution of sodium hydrogen carbonate and extracted with ethyl acetate. The organic layer was washed with a saturated $KHSO_4$ solution, a $NaHCO_3$ solution and then an aqueous sodium chloride solution. After drying with $MgSO_4$, the solvent was distilled away and the resultant crude product was subjected to silica gel chromatography to purify it. Thus, 363 mg (yield 88%) of (17R)-19,20-dehydro-17,20-dimethyl-7-thiaprostaglandin $E_1$ methyl ester was obtained in the 70 to 80% ethyl acetate-n-hexane eluate fraction.

Nuclear Magnetic Resonance ($CDCL_3$, δ (ppm)): 0.90 (3H, d, J=5 Hz), 3.60 (3H, s), 3.5~4.4 (4H, br), 5.2~5.8 (4H, m).

Infrared Absorption Spectrum (liquid film, $cm^{-1}$); 3425, 1735, 1438, 1200, 1172, 1080, 965.

Mass Spectrometric Analysis (EI, m/e); 394 (M-$H_2O$), 376 (M-$2H_2O$)

(ii) Similarly, from the (17S)-19,20-dehydro-17,20-dimethyl-11,15-bis(t-butyldimethylsilyl)-7-thiaprostaglandin $E_1$ methyl ester obtained in Example 26, (17S)-19,20-dehydro-17,20-dimethyl-7-thiaprostaglandin $E_1$ methyl ester was obtained.

Nuclear Magnetic Resonance ($CDCl_3$, δ (ppm)); 0.90 (3H, d, J=5 Hz), 33.62 (3H, s), 3.5~4.4 (4H, br), 5.2~5.2 (4H, m).

Infrared Absorption Spectrum (liquid film, $cm^{-1}$); 3420, 1738, 1438, 1200, 1170, 1080, 965.

Mass Spectrometric Analysis (EI, m/e); 394 (M-$H_2O$), 376 (M-$2H_2O$).

EXAMPLE 28

Synthesis of
(16RS)-15-deoxy-16-hydroxy-16-methyl-7-thiaprostaglandin $E_1$ geranyl ester 100 mg (0.25 mmol) of (16RS)-15-deoxy-16-hydroxy-16-methyl-7-thiaprostaglandin $E_1$ was dissolved in dry methylene chloride (1.2 ml). To this solution, 124 μl (0.72 mmol) of geraniol was added. To this mixture, 9 mg (0.072 mmol) of 4- dimethylaminopyridine and then 74 mg (0.36 mmol) of dicyclohexylcarbodiimide were added under ice cooling, and the mixture was stirred for 30 minutes and then at room temperature for 1 hour. Ethyl acetate (20 ml) was added to the mixture and the resultant mixture was Celite filtered. The filtrate was mixed with water and the mixture was shaken in a separating funnel. The aqueous layer was again extracted with ethyl acetate (20 ml), after which the combined organic layer was washed with an aqueous potassium hydrogen sulfate solution, an aqueous sodium hydrogen carbonate solution, and an aqueous solution saturated with sodium chloride, and then dried over magnesium sulfate, after which the solvent was distilled away. The resultant residue was subjected to silica gel chromatography to effect separation and purification. Thus, 70 mg (yield 52%) of (16RS)-15-deoxy-16-hydroxy-16-methyl-7-thiaprostaglandin $E_1$ geranyl ester was obtained in the hexane-ethyl acetate (1:1) eluate fraction.

Nuclear Magnetic Resonance ($CDCl_3$, δ (ppm)); 0.88 (3H, t), 1.14 (3H, s), 1.57 (3H, s), 1.67 (6H, s), 3.9~4.3 (1H, br), 4.52 (2H, d, J=7 Hz), 4.8~5.4 (2H, br), 5.61 (2H, m).

Infrared Absorption Spectrum (liquid film, $cm^{-1}$); 3400, 2960, 2940, 2860, 1740, 1450, 1160, 965.

EXAMPLE 29

(i) Determination of Antiulcerative Effect

The inhibiting effect on ulcer formation induced by indomethacin was examined by using rats. Wister male rats (7 weeks old and body weight of 220 g) were abstained from food for 24 hours except giving water and then subjected to experiments.

The sample compounds to be tested were dissolved in a phosphoric acid buffer (pH 7.4) containing 0.9% NaCl and the solution was orally administered to the rats. 30 minutes after the administration, indomethacin was orally administered to the rats at a dose of 20 mg/kg. 5 hours after the administration of the indomethacin, the rats were killed and the ulcer formation in the stomach was examined by determining the length of the ulcer formation portion under a stereomicroscope. From this measurement, the inhibition of ulcer formation by the sample compounds were calculated to determine the ED values. The results are shown in Table 1.

(ii) In vitro Blood Platelet Aggregation Inhibition Effect

The in vitro blood platelet aggregation inhibition effect of the sample compounds to be tested was examined by using rabbits. That is, blood was collected from the ear vein of native Japanese white male domestic rabbits weighing 2.5 to 3.5 kg. The collected blood was 9 parts by volume per 1 part by volume of a 3.8% sodium citrate solution. The blood was centrifuged at 1000 r.p.m. for 10 minutes. The upper layer portion was separated as PRP (rich in platelet blood plasma). The lower layer portion was further centrifuged at 2800 r.p.m. for 10 minutes to divide it into two layers. The upper layer portion was separated as PPP (poor in platelet blood plasma). The number of the platelet was diluted with PPP to 6 to $7 \times 10^3/\mu l$. After the adjustment, 25 μl of the sample compound was added to 250 μl of PRP, which was preincubated at a temperature of 37° C. for 2 minutes. Thereafter, 10 μM of ADP (final) was added to the preincubated PRP to record the variation of the transmittance by means of aggregometer. The sample compounds were dissolved in ethanol to provide 10 mg/ml.

When the activity of the sample compounds was determined, the ethanol solution was diluted with a phosphoric acid buffer (PH 7.4). The ethanol solution diluted with the buffer was left to stand at a temperature of 0° C. for 4 hours, after which the activity of the sample compounds was determined in the same manner.

The platelet aggregation inhibition was calculated by the following formula:

$$\text{Inhibition } (\%) \leq (1 - T_o/T) \times 100$$

$T_o$: the transmittance of the system to which the phosphoric acid buffer is added $T$: the transmittance of the system to which the sample compounds are added The lowest concentration of the sample compounds at which the inhibition is 50% was represented as an $IC_{50}$ value. The results are shown in Table 1.

TABLE 1

| Compound | Antiulcerative effect $ED_{50}(\mu g/kg)P.O$ | Anti-platelet aggregation effect $IC_{50}(\mu g/ml)$ |
|---|---|---|
| Compound of this invention | 10 | 17 |

Comparative compound

TABLE 1-continued

| Compound | Antiulcerative effect ED$_{50}$(μg/kg)P.O | Anti-platelet aggregation effect IC$_{50}$(μg/ml) |
|---|---|---|
| (structure with COOCH$_3$, S, OH, cyclopentanone) | 300 | >100 |
| (structure with COOCH$_3$, S, HO, OH, H, cyclopentanone) | 35 | 0.004 |

As is apparent from Table 1, the compounds of the present invention are those having especially strong antiulcerative effect.

EXAMPLE 30

Determination of Effect against Ethanol Ulcer

SD type male rats (7 weeks old and body weight of 220 g) were abstained from food for 24 hours except giving water and then subjected to experiments.

The sample compound to be tested was dissolved in a phosphoric acid buffer (pH 7.4) containing 0.9% NaCl and the solution was orally administered to the rats. 30 minutes after the administration, 75% ethanol was orally administered to the rats at a dose of 1 ml/kg. One hour after the administration of the ethanol, the rats were killed and the ulcer formation in the stomach was examined by determining the length of the ulcer formation portion under a stereomicroscope. From this measurement, the inhibition of ulcer formation by the sample compound was calculated to determine the ED$_{50}$ value. The result is shown in Table 2.

TABLE 2

| Compound | Antiulcerative effect ED$_{50}$(μg/kg)P.O |
|---|---|
| Compound of this invention (structure with COOCH$_3$, S, HO, OH) | 18 |

CAPABILITY OF EXPLOITATION IN INDUSTRY

The 7-thiaprostaglandins E$_1$ of the present invention have interesting physiological activities and can be used for the prevention and/or treatment of various diseases such as digestive organ diseases, e.g., a duodenal ulcer and a gastric ulcer; liver diseases, e.g., hepatitis, toxipathic hepatitis, hepatic coma, hepertrophy of the liver, and hepatocirrhosis; pancreas, e.g., pancreatitis; arinary diseases, e.g., diabetos kidney diseases, acute kidney insufficiency, cystitis, and urethritis; respiratory diseases, e.g., pneumonia and bronchitis; incretion diseases; immunity diseases; toxicosis, e.g., alcohol poisoning and carbon tetrachloride poisoning and low blood pressure.

The 7-thiaprostaglandins E$_1$ of the present invention are especially useful for the treatment and prevention of digestive organ diseases such as a duodenal ulcer and a gastric ulcer.

We claim:

1. 7-thiaprostaglandins E$_1$ which are compounds represented by the following formula (I) or their enantiomers or mixtures thereof in any ratio:

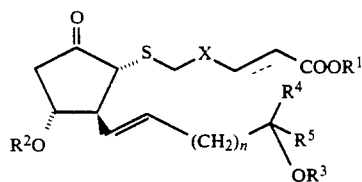

wherein R$^1$ represents a hydrogen atom, a C$_1$-C$_{10}$ alkyl group, a C$_2$-C$_{20}$ alkenyl group, a substituted or unsubstituted phenyl group, a substituted or unsubstituted C$_3$-C$_{10}$ cycloalkyl group, a substituted or unsubstituted phenyl (C$_1$-C$_2$) alkyl group, or one equivalent cation R$^2$ and R$^3$, which are the same or different, represent a hydrogen atom, a tri(C$_1$-C$_7$) hydrocarbon silyl group, or a group forming an acetal linkage together with an oxygen atom of a hydroxyl group; R$^4$ represents a hydrogen atom, a methyl group or a vinyl group; R$^5$ represents a linear or branched C$_3$-C$_8$ alkyl group, a linear or branched C$_3$-C$_8$ alkenyl group, a linear or branched C$_{36}$ l-C$_8$ alkynyl group, a substituted or unsubstituted phenyl group, a substituted or unsubstituted C$_3$-C$_{10}$ cycloalkyl group, or a linear or branched C$_1$-C$_5$ alkyl group substituted with a C$_1$-C$_6$ alkoxy group, a substituted or unsubstituted phenyl group, a substituted or unsubstituted phenoxy group or a substituted or unsubstituted C$_3$-C$_{10}$ cycloalkyl group; x represents an ethylene group, a vinylene group or an ethynylene group; n represents 0; the expression ⫽ represents an ethylene group or a vinylene group; provided that, when x is an ethylene group, R$^5$ is a linear or branched C$_3$-C$_8$ alkenyl group; wherein the substituent of the each substituted group mentioned above is a halogen atom, a hydroxy group, a C$_2$-C$_7$ acyloxy group, a C$_1$-C$_4$ alkyl group which may be substituted with a halogen atom, a C$_1$-C$_4$ alkoxy group which may be substituted with a halogen atom, a nitrile group, a carboxyl group of a (C$_1$-C$_6$) alkoxycarbonyl group.

2. The 7-thiaprostaglandins E$_1$ according to claim 1 wherein R$^1$ is a hydrogen atom, a C$_1$-C$_{10}$ alkyl group, a C$_2$-C$_{20}$ alkenyl group or one equivalent cation.

3. The 7-thiaprostaglandins E$_1$ according to claim 1 wherein R$^5$ is a butyl group, a pentyl group, a 1-methyl-1-butyl group, a 2-methyl-1-butyl group, a cyclopentyl group, a cyclohexyl group or a phenyl group.

* * * * *